United States Patent [19]

Walters et al.

[11] 4,288,695

[45] Sep. 8, 1981

[54] COMPUTERIZED TOMOGRAPHIC SCANNER WITH SHAPED RADIATION FILTER

[75] Inventors: Ronald G. Walters, Aurora; Roland W. Carlson, Lyndhurst, both of Ohio

[73] Assignee: Technicare Corporation, Cleveland, Ohio

[21] Appl. No.: 29,877

[22] Filed: Apr. 13, 1979

[51] Int. Cl.³ .................... G01N 23/02; G21F 3/02
[52] U.S. Cl. ................... 250/445 T; 250/510
[58] Field of Search ............... 250/445 T, 510, 505, 250/362 S

[56] References Cited

U.S. PATENT DOCUMENTS

| | | |
|---|---|---|
| 3,717,768 | 2/1973 | Edholm et al. ............ 250/510 |
| 3,755,672 | 8/1973 | Edholm et al. . |
| 3,937,963 | 2/1976 | Hounsfield . |
| 3,940,625 | 2/1976 | Hounsfield . |
| 3,946,234 | 3/1976 | Hounsfield . |
| 3,956,633 | 5/1976 | Hounsfield . |
| 3,965,357 | 6/1976 | Hounsfield ............ 250/510 |
| 3,996,467 | 12/1976 | Froggatt et al. . |
| 3,999,073 | 12/1976 | Hounsfield et al. . |
| 4,006,361 | 2/1977 | Schriber ............ 250/510 |
| 4,010,371 | 3/1977 | LeMay . |
| 4,028,554 | 6/1977 | Hounsfield . |
| 4,069,422 | 1/1978 | Hounsfield . |
| 4,084,094 | 4/1978 | Froggatt . |

*Primary Examiner*—Bruce C. Anderson
*Attorney, Agent, or Firm*—Fay & Sharpe

[57] ABSTRACT

The invention comprises a shaped filter and a filter correction circuitry for computerized tomographic scanners. The shaped filter is a generally U-shaped block of filter material which is adapted to be mounted between the source of radiation and the scan circle. The U-shaped block has a parabolic recess. The filter material may be beryllium, aluminum, sulphur, calcium, titanium, erbium, copper, and compounds including oxides and alloys thereof. The filter correction circuit comprises a first filter correction profile adding circuit for adding a first scaler valve to each intensity valve in a data line. The data line is operated on by a beam hardness correction polynomial. After the beam hardness polynomial correction operation, a second filter correction circuit adds a second filter correction profile consisting of a table of scalor values, one corresponding to each intensity reading in the data line.

20 Claims, 3 Drawing Figures

COMPUTERIZED TOMOGRAPHIC SCANNER WITH SHAPED RADIATION FILTER

BACKGROUND OF THE INVENTION

This application pertains to the art of tomographic image reconstruction and more particularly, to computerized tomographic scanners for medical diagnostic and other uses.

The invention is particularly applicable to medical diagnostic computerized axial tomographic scanners and will be described in particular reference thereto. It will be appreciated however, that the invention has broader application such as industrial flaw detectors.

Generally, a tomographic scanner comprises a scan circle to which an object to be examined may be placed. Movably mounted about the scan circle is a source of radiation so mounted and positioned that it can irradiate a planar slice of a scan circle from a number of directions within a plane. Positioned opposite the scan circle from the source of radiation is one or more radiation detectors which receive radiation which has traversed the scan circle. From the variations in the radiation intensity detected along various known paths to the scan circle, a processing unit reconstructs an image of the planar slice of the object in the scan circle. The intensity of the radiation received by each detector is a function of the intensity of the source, the mass absorption coefficient of each material between the source and the detector, and the path length of each material between the source and the detector.

The mass attenuation coefficient of almost all materials is a function of the energy of the radiation. Thus, for polychromatic radiation, the amount of attenuation is different for each of the many energy components which make up the polychromatic spectrum. This energy dependent variation in the attenuation coefficient causes problems in prior art scanners because it produces nonlinearities which distort the reconstructed image.

Another problem with prior tomographic scanners has been the dosage level with which they irradiate the patient or other object in the scan circle. Generally, the intensity of the radiation produced by the source is constant across the scan circle. Radiation of the same intensity is aimed to traverse all parts of the scan circle including the relatively long paths near the center and the relatively short paths near the periphery. Because the thickness of the object and the scan circle is generally thinner near the periphery, the radiation traverses a shorter path length than it would if if were passing through the center of the scan circle. When the path length is shorter, a lower intensity of radiation is required for reconstructing the image. Accordingly, when the entire scan circle is subject to radiation of the same intensity, part of the patient is subject to more radiation than is necessary.

Another problem with the prior art tomographic scanners has been their inability to compensate for various different nonlinearities introduced by different filter materials. The change of the polychromatic spectrum caused by different filter materials has been found to change the tomographic scanner's ability to differentiate among various materials which comprise the object or patient being examined.

In the past, others have tried to alleviate these problems by using generally flat filters. Others have used water equivalent filters which are shaped so that radiation from the radiation source passing through the water equivalent filter and the scan circle traverse an equivalent amount of water regardless of which part of the scan circle they traverse. Water has been selected because when human patients are examined, the mass attenuation coefficient of the human body is generally the same as the mass attenuation coefficient of water.

The present invention contemplates a tomographic scanner which overcomes all of the above problems and others. The present invention provides a tomographic scanner which is as simple to operate as prior scanners, but can compensate for non-linearities produced by filters of nearly any material and configuration without complex correction calculations or tune-up procedures.

In accordance with the present invention, there is provided an apparatus for reconstructing an image of a region of an object positioned within a scan circle. The apparatus comprises a source of radiation having a polychromatic spectrum for irradiating the scan circle with radiation from a plurality of directions. It also includes at least one radiation detector mounted and positioned to receive radiation from the source which has traversed the scan circle along a plurality of paths. A radiation filter is positioned between the source of radiation and the detector. A data collection means collects from the at least one detector data indicative of the intensity of radiation received by each of the radiation detectors along the plurality of paths and organizes the collected data into data lines. A beam hardness correction means adjusts the data lines for nonlinearities introduced by the polychromatic spectrum of radiation from the source of radiation. A filter correction means adjusts the data lines for nonlinearities introduced by alterations to the polychromatic spectrum by the radiation filter. The beam hardness correction means and the filter correction means are operatively connected with the data collection means. A reconstruction means which reconstructs the data lines into a representation of an image of the region is connected to the beam hardness correction means and the filter correction means for receiving data lines which have been adjusted thereby.

In accordance with a more limited aspect of the invention, the filter correction means comprises a first altering means for altering the data lines by adding a value thereto before the data line is adjusted by the beam hardness correction means and a second adjusting means for adding a value to the data line after correction by the beam hardness correction means.

In accordance with another more limited aspect of the invention, the radiation filter is constructed of a block of beryllium, aluminum, sulfur, calcium, titanium, erbium, or copper or compounds or alloys thereof with a parabolic recess.

A principal advantage of the invention is that filters of nearly any shape and material may be used in a tomographic scanner.

Another advantage of the present invention is that it reduces dosage received by the patient without degrading the reconstructed image.

A further advantage of the present invention is that improved reconstructed images are achieveable with the substitution of different radiation filter materials.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof.

DESCRIPTION OF THE PREFERRED EMBODIMENT

Reference is now made to the drawings wherein the showings are for the purpose of illustrating the preferred embodiment of the invention and not for the purpose of limiting it. The device includes a scan circle A into which a region of the object to be examined may be placed. Adjacent the scan circle is a source B of radiation for irradiating the object within the scan circle. Oppositely disposed from the source of radiation is a detector means C for detecting radiation from the source which has traversed the scan circle along a plurality of paths. A radiation filter D is removably mounted between the scan circle and the source to alter the polychromatic spectrum, partially attenuate the radiation, and reduce patient dose. Connected with detector means C is a data collection means E for collecting data indicative of intensity of radiation received by each detector of radiation detector means C and data indicative of the path through the object which the radiation traversed. The collection means organizes the collected data into data lines. Each data line is indicative of the relative radiation intensity along each path of a group of paths spanning the scan circle. A beam hardness correction means F adjusts the data lines to correct nonlinearities introduced by the polychromatic spectrum of the radiation from the source. A filter correction means G further adjusts the data lines to correct any nonlinearities introduced by alterations to the polychromatic spectrum caused by radiation filter D. A reconstruction means H reconstructs the adjusted data lines into a representation of an image of the region of the object examined.

Figure 1:
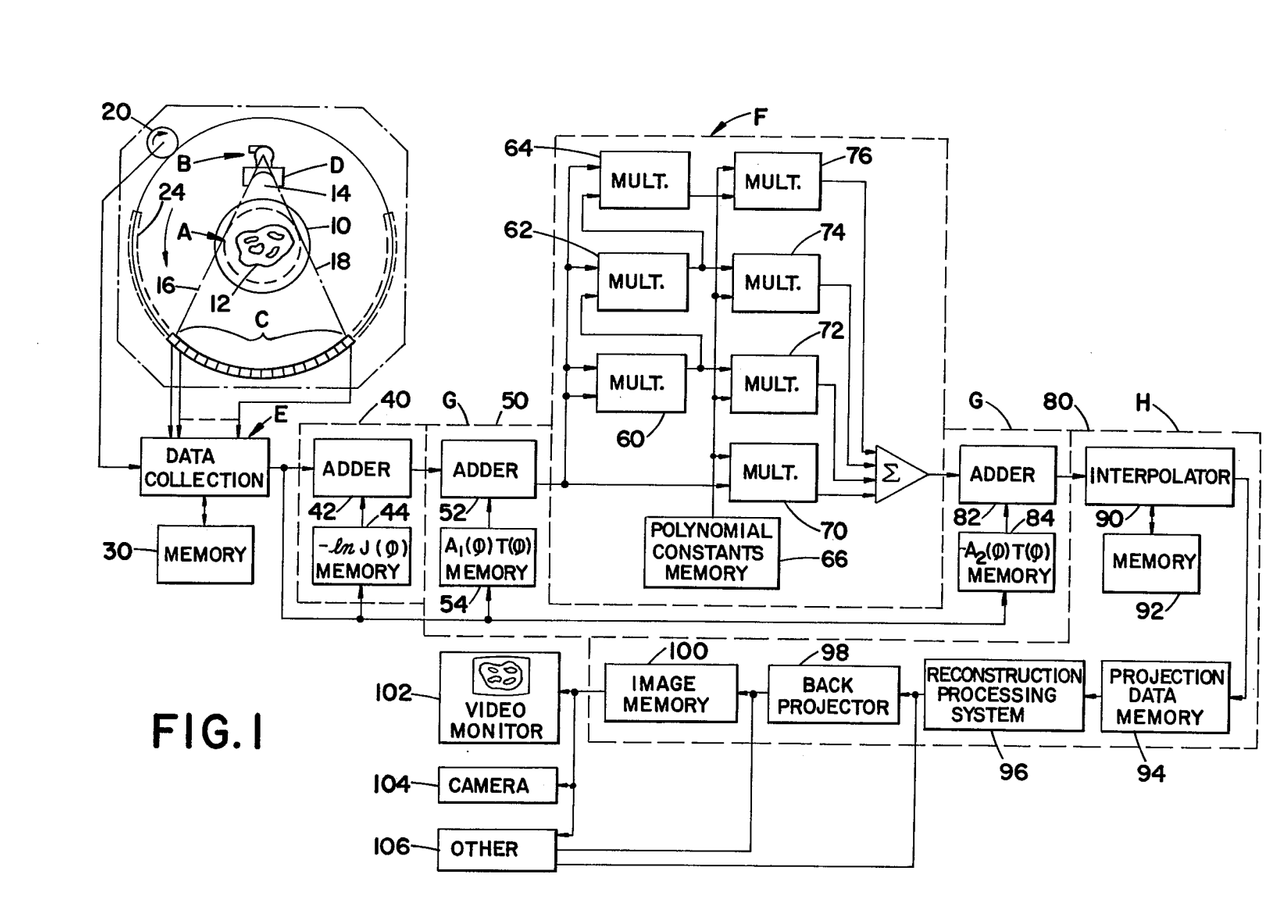
FIG. 1 is a block diagram of an apparatus for reconstructing an image in accordance with the present invention.

FIG. 1 illustrates a rotating fan beam-type tomographic scanner. However, traverse and rotate or other types of tomographic scanners can be used in conjunction with the present invention.

In the FIG. 1 embodiment a cylindrical member 10 acts to support the object to be examined and defines the maximum size of the scan circle. By way of illustration, an object 12 is illustrated within the scan circle A. A source of radiation B such as an x-ray tube is mounted for rotational movement about cylinder 10. The x-ray tube contains the appropriate apertures or the like to constrain the radiation generated therein to a substantially fan-shaped swath of radiation 14. The extremes of the fan of radiation 16 and 18 are tangent with the scan circle. By adjusting the spread of fan 14 the size of the scan circle can be selected. A rotating means 20 rotates the source of radiation and provides a signal indicative of the angular position of the source relative to the scan circle. Detector means C may be an arc of detectors such as detector 22. The detectors span a length corresponding to the divergence of the fan of radiation for largest selectable scan circle. Each of the detectors may, for example, be a scintillation crystal such as bismuth germanium oxide optically connected with a photomultiplier tube. Variations in the intensity of radiation impinging upon the scintillation crystal cause voltage outputs of the photomultiplier tubes to vary by a corresponding amount. Radiation filter D is positioned between the source of radiation and the scan circle. The filter could also be placed between the scan circle and detector means C. However, such a placement would reduce the radiation intensity without reducing the patient dose. The arc of detectors are stationary but may alternately be rotated with the source of radiation B. If the detectors are stationary, the arc should extend as shown in phantom, or alternately 360 degrees around the scan circle.

Data collection means E receives the indication of the intensity received by each of the detectors and an indication of the angular position of the radiation source. From this information, data collection means can determine the specific path through the scan circle which each intensity sampling of each of the detectors represents. In the preferred embodiment, the intensity from each one of the detectors is sampled for each tenth of a degree of rotation of source B. Corresponding to each detector position are a series of intensity values which correspond to one of a fan-shaped array of paths through the scan circle, converging at the position of that detector. The data collection means forms the intensity data into a data line corresponding to each detector fan. Each data line is uniquely described by the angular position of its apex about the scan circle. Data within each data line is addressed by the relative angular position of the path within the detector fan of radiation paths which correspond to that data line. A memory 30 may store temporarily parts of some of the data lines until all the intensities needed to construct the data line are collected.

Each data line is conveyed to an air correction means 40 for correcting the data lines for the attenuation of radiation between the source and detector caused by air and angular variations in source intensity. This means includes an adding means 42 for adding to each intensity within the data line a value from a table in memory 44. The values within the table are a series of scalers each corresponding to an angle within the detector fan. Each data line may be conceptualized as a curve plotting of the logarithm of the intensity received versus the angle within the detector fan. The table of values 44 may be considered to be another curve plotting the amount of correction versus angular position within the detector fan. Adding means 42 adds these two curves together to adjust the data lines for nonlinearities caused by the radiation passing through air.

The filter correction means G has a first altering means 50 for altering the data lines before the beam hardness correction is made. First altering means 50 includes an adding means 52 for adding scaler values from a first memory means 54 to each intensity measurement in the data line. Each scaler value within the first memory means 54 is an indication of an amount of correction as a function of the angular position within the detector fan. Again, adding means 52 may be conceptualized as adding a correction curve of the amount of correction versus angle within the detector fan to the data line curve.

Beam hardness correction means F may be embodied in several ways. Conventionally, beam hardness correction is achieved with a polynomial operation on the data lines. Although a polynomial of any order may be used, a fourth order polynomial is illustrated in the preferred embodiment. The polynomial operation is carried out in a point-by-point operation across the data line. The intensity value for the first angular position in the detector fan is conveyed to a multiplying means 60 which multiplies the value by itself to form the square of that value. A second multiplying means 62 multiplies the square of the value from multiplying means 60 by the value again to form the cube. Multiplying means 64 multiplies the cube of the value from multiplying means 62 by the value again to raise the value to the fourth power. A memory 66 stores a table of four polynomial constants which are derived in the periodical tune-up process which will be described below. A multiplying means 70 multiplies the intensity value by a first constant. A second multiplying means 72 multiplies the square of the intensity value by a second constant; a third multiplying means 74 multiplies the cube of the intensity value by a third constant; and a fourth multiplying means 76 multiplies the fourth power of the intensity value by a fourth constant. The sum of the products from multiplying means 70, 72, 74 and 76 are added by a summing means 78 to complete the polynomial operation on the first angular position of the data within the data line. This operation is repeated for the intensity data at each angular position within the data line to produce a data line with the polynomial correction for beam hardness.

The filter correction means G further includes a second altering means 80. The second altering means 80 includes a second adding means 82 which adds scaler values from a second memory means 84 to the data line. Like first memory means 54, second memory means 84 stores a table of scaler values, one corresponding to each of the angular positions within the detector fan. Again, adding means 82 may be conceptualized as adding a curve of amount of correction versus angular position within the detector fan to the data line curve. The beam hardness, air and filter correction means thus, perform a correction which is described mathematically as:

$$D(\phi) \simeq P[I(\phi) - \ln J(\phi) + A_1(\phi)T(\phi)] - A_2(\phi)T(\phi) \quad (1)$$

Where $D(\phi)$ represents a corrected data line, P represents the polynomial correction of the beam hardness correction means, $I(\phi)$ represents the data line from data collection means E, $-\ln J(\phi)$ represents the values stored in memory 44, $A_1(\phi)T(\phi)$ represents the table of values stored in first memory means 54, and $-A_2(\phi)T(\phi)$ represents the table of values stored in second memory means 84. These mathematical variables and the terminology are chosen for consistency with the terminology of the theory section below.

The corrected data lines are then conveyed to reconstruction means H. The details of a suitable reconstruction means H are set forth in U.S. application Ser. No. 32,452, filed Apr. 23, 1979, now allowed, which is a divisional of U.S. application Ser. No. 838,084 filed Sept. 30, 1977, now abandoned the disclosure of which is incorporated herein by reference. Reconstruction means H in a preferred embodiment includes an interpolator 90 for expanding the intensity values corresponding to the discrete angular positions into data corresponding to equal tangents within the detector fan. A memory means 92 is used for temporary storage of data during this interpolation process. Each interpolated data line is then stored temporarily in a projection data memory 94. A reconstruction processing system 96 serially processes each data line with the algorithms as explained in the above referenced patent application. Serially, data lines from the reconstruction processing system are backprojected by a backprojection means 98 into an image memory 100 in the manner explained in the above patent of referenced patent application. The image memory may be pictured as a rectangular array of memory elements each of which corresponds to one of a rectangular array of elements within the object examined. During the backprojection process, values are accumulated in each memory element corresponding to the radiation attenuation characteristics of the corresponding element in the examined object. The values within the image memory 100 may be displayed on a video monitor 102. Alternately, the values within the image memory 100 may be transformed into a photographic image with an electronic data camera 104 such as the DELTAMAT camera sold by Ohio-Nuclear, Inc. of Solon, Ohio. Further, other processing means 106 may operate on this data. For example, a tape memory can record the information in the image memory or it may record the data lines before or after backprojection.

Figure 2:
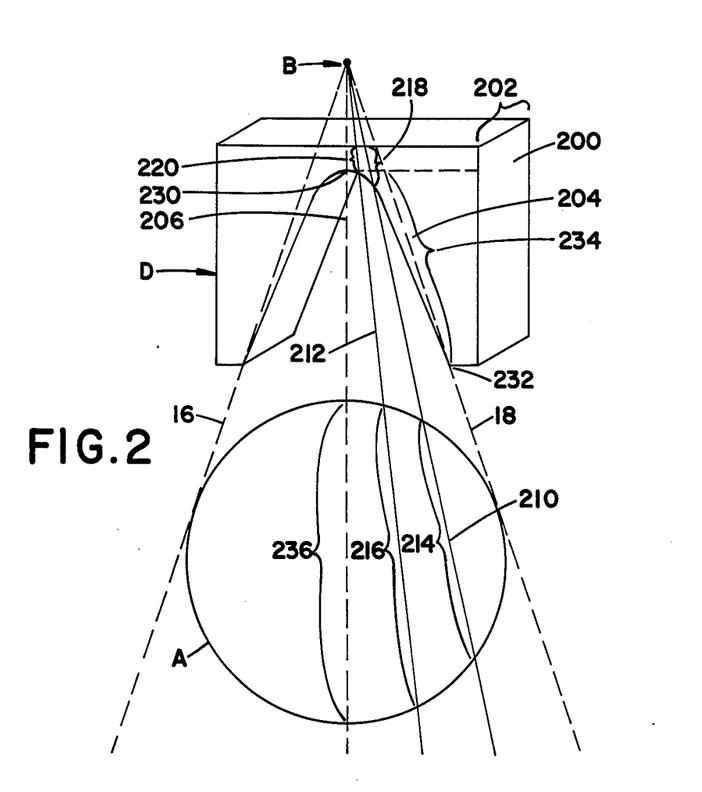
FIG. 2 is a view of a radiation filter in accordance with the present invention.

FIG. 2 illustrates a more detailed description of the radiation filter D of the preferred embodiment. The filter is constructed from a block 200 of a filter material which alters the radiation spectrum and attenuates the radiation. The body has a width 202 comparable to the maximum thickness of the fan beam of radiation to be used for making diagnostic examination of the object in the scan circle. The body has a parabolically shaped slot or recess 204 formed in the face to be disposed opposite the source of radiation. The parabolic recess has a central axis 206. In a tomographic scanner, the filter is disposed in such a manner that the parabolic central axis 206 lies along a line extending between the center of the source of radiation B and the center of scan circle A. This axis is the same as the central axis of the fan beam of radiation. The parabolic recess further has a base dimension 208 which is generally perpendicular to the axis. The base 208 is dimensioned so that the fan beam just spans it. If a smaller scan circle is to be examined and the fan beam angle is contracted, the filter may be shifted relative to the source of a fan beam until the base dimension 208 is coincident with edges 16 and 18 of the fan beam.

The depth of the parabolic slot or recess may be determined in various manners. In the preferred embodiment, the depth is such that radiation after passing through the filter body and a water phantom, emerges with a generally constant intensity across the fan beam or a lower intensity adjacent edges 16 and 18. One manner of determining the dimensions of the recess is to project lines from the center of the source through the filter and the scan circle. For example, a projection line 210 extends from the center of the source through the filter and the scan circle. A second projection line 212 is illustrated also projecting from the source through the scan circle. It will be appreciated that the path length 214 through the scan circle of line 210 is less than the path length 216 through the scan circle of line 212. To determine the shape of the recess, these path lengths and numerous other similar path lengths across the scan circle are subtracted from a nominal filter thickness value which is greater than the diameter of the scan circle. The thickness of the filter along each projection line is determined such that the corresponding path lengths through the filter, are equal to the difference between the nominal filter thickness and the path length through the scan circle. For example, path length 218 corresponding to path 210 and path length 220 corresponding to path 212, are equal respectively to the differences between the nominal thickness and the path lengths 214 and 216. This determines the relative shape of the recess. The shape of the recess thus determined is generally parabolic. Excellent results have been obtained by approximating the exact determined recess shape with a parabola. Some variations from a parabola and other similar shapes may also provide adequate results. The exact physical dimensions or size of the parabola may be reduced proportionately as the filter material becomes more absorptive of radiation.

A parabola is generally defined by the equation $$y = ax^2 \tag{2a}$$

From the origin 230 and another point 232 on the parabola and selecting the parabola to provide the same attenuation along path 234 as path 236, it can be shown that:

$$a = \frac{2\alpha R \cos\theta/2}{\beta \left( \frac{2\alpha R}{\beta} \sin\theta/2 + r \tan\theta/2 \right)^2} \tag{2b}$$

where R is the scan circle radius, r is the distance from the fan apex to the origin, $\theta$ is the fan angle, $\alpha$ is the attenuation coefficient of water, and $\beta$ is the attenuation coefficient of the filter. A value for "a" for an aluminum filter which produces a generally constant intensity distribution is 0.50. Increasing the strength of the parabola by increasing "a" reduces the intensity of radiation emerging from near the peripheral edges of the scan circle. The reduction in the intensity of the radiation near the periphery of the scan circle reduces the image quality around the periphery of the reconstructed image. However, the stronger parabola decreases the patient dosage. Often the center of the image portrays the primary area of medical interest. Accordingly, increasing the strength of the parabola by a factor of two or more has been found to reduce patient dosage significantly without significantly affecting the medical utility of the reconstructed image.

Filter materials of varying types may be used. Generally, filter materials with a higher atomic number attenuate the radiation intensity more than materials with a lower atomic number. Different filter materials as indicated above, affect different parts of the polychromatic x-ray spectrum in different manners. Thus, it is often hard to preduct whether a filter material will produce an image with good white/gray contrast, or with good bone edge definition or with other desirable properties of tomographic images. The present invention enables the trial of various potential filter materials with relative simplicity. The following filter materials have been tried and found to be advantageous: berrylium oxide, aluminum, sulphur, calcium oxide, titanium, erbium oxide and copper. Materials having a K-absorption edge near 57.5 KEV, such as compounds of erbium have the advantage of producing a band pass effect.

TUNE-UP PROCEDURE

The tables of values stored in memory 44 and 66 are obtained in conventional tune-up procedures. The values for table 44 are determined by performing a tomographic scan of the scan circle when it is empty, except for air, also known as an air scan. The values are selected such that when added to the average intensity value at the corresponding angular position, $\phi$, in the detector fan the resultant image is uniform. In this manner, the values of table 44 compensate for the absorption of air and the different path lengths through air that rays at different angular positions of the fan beam of radiation encounter. To determine the values of the polynomial constants for memory 66 a second scan is done with a reference material filling the scan circle. The reference material is chosen to have a mass absorption coefficient substantially the same as the object to be examined. For human patients, the reference material is conventionally water. Because the mass absorption coefficient for water is not linear, but rather a function of energy, a nonlinear correction is made. Conventionally, a polynomial correction is made. In the preferred embodiment, the polynomial correction is a fourth order polynomial. However, a higher order polynomial would give more accuracy, while a lower order polynomial would reduce computation time. To obtain the values of the polynomial constants $C_1$, $C_2$, $C_3$ and $C_4$, a tomographic scan is taken when the scan circle is filled with water, also known as a water phantom. The constants for the polynomials are iteratively adjusted until the resultant image is uniform.

The values for first memory means 54 $A_1(\phi)T(\phi)$ and the values in the second memory 84, $A_2(\phi)T(\phi)$ can be determined empirically, theoretically or with a combination of the two techniques.

The preferred method of determining the values in the first and second memory means involves a combination of empirical measurements and theoretical calculations. This method requires only two scans. The first step is to obtain the mass absorption coefficient for water, $\alpha$ ($\epsilon$), the mass absorption coefficient for the filter material $\beta$ ($\epsilon$), the source spectrum $I(\epsilon)$, a mathematical description of the filter shape $T^*(\phi)$, the scaler of the nominal mass absorption coefficient of the filter to the nominal mass absorption coefficient of water $B^*$, the density of the filter d, the scan circle radius R, the unfiltered correction polynomial from water P, and the intensity measurements from an air scan with the filter in place averaged over all views $I_f(\phi)$. The mass absorption coefficients for water and the filter material, the ratio of the mass absorption coefficients, and the density of the filter can all be measured empirically or determined from physics tables. The spectrum may also be measured empirically or can be calculated from the beam hardness polynomial. The mathematical description of the filter shape and path length as a function of fan angle may be measured or calculated mathematically from the known filter shape. The scan circle radius may be measured. The water polynomial values may be obtained from a conventional tune-up procedure described above, and the air scan with filter values may be obtained by scanning the scan circle when it is empty except for air with a filter in place.

Step 2 is to calculate a set of dummy variables $q(\phi)$, $r(\phi)$ and $s(\phi)$ each of which is defined as follows:

$$q(\phi) = \ln \int_0^\infty I(\epsilon) e^{-\beta(\epsilon) dT^*(\phi)} d\epsilon \tag{3a}$$

$$r(\phi) = \ln \int_0^\infty I(\epsilon) e^{-\alpha(\epsilon)[2R - dB^*T^*(\phi)]} d\epsilon \tag{3b}$$

$$s(\phi) = \ln \int_0^\infty I(\epsilon)e^{-\alpha(\epsilon)[2R - dB^*T^*(\phi)] - \beta(\epsilon)T^*(\phi)} d\epsilon \quad (3c)$$

Step 3 is to obtain the roots designated $v(\phi)$ for each $(\phi)$ for the polynomial of the beam hardness correction means F when $r(\phi)$, from equation 3(b) above, is used as the input data to the beam hardness correction means, i.e. the roots of equation:

$$0 = -P_{[r(\phi)]} + \sum_{M=0}^{3} v^M(\phi) \sum_{N=1}^{4-M} \frac{(M+N)!}{M!N!} P_{[M+N]}(s^N(\phi) - q^N(\phi)) \quad (4)$$

It will be appreciated that polynomials of a greater order may be used to increase accuracy, or polynomials of a lesser order may be used to reduce the calculations necessary for determining the roots. Determination of the roots is done with a conventional iterative process.

Step 4 is to calculate the ratio of $A_2(\phi)$ to $A_1(\phi)$:

$$\frac{A_2(\phi)}{A_1(\phi)} = \frac{P_{[q(\phi) - v(\phi)]}}{v(\phi)} \quad (5)$$

The polynomial P is a beam hardness correction polynomial where $q(\phi) - v(\phi)$ are the input variables and $v(\phi)$ are the roots of the polynomial determined in step 3 above.

Step 5 is to obtain roots $y(\phi)$ for each of the $\phi$ of the polynomial expression:

$$0 = C_4 y^4(\phi) + C_3 y^3(\phi) + C_2 y^2(\phi) + \left(C_1 - \frac{A_2(\phi)}{A_1(\phi)}\right) y(\phi) + \frac{A_2(\phi)}{A_1(\phi)} (\ln J(\phi) - I_f(\phi)) \quad (6)$$

Where $C_1$ through $C_4$ are polynomial coefficients from memory means 66. Again, a higher or lower order polynomial than the fourth order polynomial of the preferred embodiment may be used.

Step 6 is to determine the first correction profile $A_1(\phi)T(\phi)$ to provide values for first memory means 54. The first profile, $A_1(\phi)T(\phi)$ is:

$$A_1(\phi)T(\phi) = y(\phi) + 1 \, nJ(\phi) - I_f(\phi) \quad (7)$$

It will be seen that $y(\phi)$ is obtained from step 5 above; $1 \, nJ(\phi)$ is obtained from the air scan without the filter in place; and $I_f(\phi)$ is obtained from an air scan with the filter in place.

Step 7, the last step, is to obtain a second profile $A_2(\phi)T(\phi)$:

$$A_2(\phi)T(\phi) = \frac{A_2(\phi)}{A_1(\phi)} (A_1(\phi)T(\phi)) \quad (8)$$

The ratio of $A_2(\phi)$ to $A_1(\phi)$ is obtained from step 4 and the value of $A_1(\phi)T(\phi)$ is found in the preceeding step.

It can be seen then, that this method determines the two correction profiles for memory means 54 and 84 by measuring the radiation intensity received by the detectors from a scan made with the filter in place and a scan made with the filter removed. This method mathematically simulates the results that would be obtained with a water phantom in place. Alternately, scans may be taken with the water phantom in place and the empirical data used instead. The empirical data may be more accurate when the water phantom is precisely centered in the scan circle. The present method, however, illeviates the necessity of centering a water phantom with great accuracy.

A second method that may be used requires four scans—an air scan with the filter in place and removed and a water phantom scan with the filter in place and removed. This method is much more dependent on empirical data than the preceeding method, and accordingly, is more tuned to minor system variations.

The first step of the second method is to obtain the polynomial from the beam hardness correction means obtained from the water scan without a shaped filter $P_n$, the detected intensity of the air scan with the shaped filter in place $I_f(\phi)$, the detected intensity of the air scan of with the shaped filter out $1 \, nJ(\phi)$, the detected intensity of the water phantom with the filter in place $I_{fw}(\phi)$, and the intensities detected with the water phantom and the water filter removed $I_w(\phi)$.

Step 2 is to calculate the values of q, r and s which are related to but not exactly the same as the dummy variables q, r and s of the first method. These are calculated according to the formulas:

$$q(\phi) = I_f(\phi) - 1 \, nJ(\phi) \quad (9a)$$

$$r(\phi) = I_w(\phi) - 1 \, nJ(\phi) \quad (9b)$$

$$s(\phi) = I_{fw}(\phi) - 1 \, nJ(\phi) \quad (9c)$$

It is seen that the values of dummy variables q, r and s are merely differences between various pairs of the four scans.

Step 3 is to obtain the roots $v(\phi)$ for each $v(\phi)$ of the polynomial expression:

$$0 = P_{[r(\phi)]} + \sum_{M=0}^{K-1} v^M(\phi) \sum_{N=1}^{K-M} \frac{(M+N)!}{M!N!} [C_{[M+N]}(s^N(\phi) - q^N(\phi)] \quad (10)$$

where K is the order of the polynomial and $C_n$ are the coefficients of the polynomial. Polynomial P is the polynomial from the beam hardness correction means. In the prefered embodiment, this is a fourth order polynomial though other orders may be used.

Step S4 is to obtain the first profile for first memory means 54:

$$A_1(\phi)T(\phi) = v(\phi) \quad (11)$$

The roots $v(\phi)$ determined in step 3 thus, form the first profile.

Step 5 is to determine the second profile:

$$A_2(\phi)T(\phi) = P_{[q(\phi) - v(\phi)]} \quad (12)$$

This is obtained by taking the value of $q(\phi)$ from step 2 and the roots $v(\phi)$ from step 3 and using the difference as the input to the beam hardness correction polynomial.

Numerous other methods may be used to determined the first and second filter correction profiles. Further, various simplifications and approximations may be used in appropriate circumstances to simplify the above methods. Other methods will become apparent from reading and understanding the theory section below.

Theory

This section presents the theory behind the above presented relationships is presented to provide a greater understanding of the invention, its scope, and equivalents. As indicated above, shaped filters can provide a superior quality image from tomographic scanners. Noise in the signals obtained is proportional to the inverse square of the number of radiation photons detected. Patient dose, on the other hand, is related to the number of photons and their energies, increasing linearly with the former and decreasing nonlinearly with the latter to about 60 KEV. Flat filters, e.g., aluminum, have helped reduce dose by eliminating low energy photons which contribute very little, if any to the detected signal. As set forth above, a shaped filter material can further reduce the skin dosage which a patient receives by a significant amount. The choice of filter material used has significant considerations to both the quality of the image and various mechanical considerations, such as physical size.

Further, as set forth above, the spectral distribution of the polychromatic radiation affects the contrast of the resultant tomographic image. Thus, it is desirable to experiment with numerous filter materials to obtain images with various spectral distributions. Of particular interest, are materials which have a K absorption edge near 60 KEV, such as erbium. These materials exhibit a band pass effect.

Heretofore, tomographic scanners have provided a correction for the nonlinearities caused by the energy dependent mass attenuation coefficient of the object examined. For medical diagnostic application, this correction is approximated as a mass attenuation coefficient of water. If water equivalent filters are added, a DC offset signal is added to the conventional correction. This enables the use of filters of LEXAN and other water equivalent materials. However, the prior art scanners lack the ability to correct the nonlinearity caused by interchanging filters of varying materials and shapes.

The detector signal is a logarithm of an integral over all energies of the polychromatic x-ray spectrum. If the beam were monochromatic the signal would be linearly related to the density, path length, and mass absorption coefficient of the material being scanned. However, the mass absorption coefficient is energy related. Accordingly, with a polychromatic radiation beam the detected signal has an inherent nonlinearity caused by the integration over all energies prior to the log operation.

Most soft tissues have a mass absorption coefficient which is essentially the same as water. Other materials such as bone and potential filter materials differ significantly from water in the energy dependent behavior of the mass absorption coefficient. For water-like objects, the detector output may be described mathematically as:

$$I(\phi) = \ln \int_0^\infty I^o(\epsilon) J(\phi) e^{-\alpha(\epsilon)_o \int^T D'(t,\phi) dt} d\epsilon \quad (13)$$

where $I^o(\epsilon)$ is the normalized intensity spectra of the source combined with the spectral response of the detector, $I(\phi)$ is the detected intensity at $\phi$, $J(\phi)$ is the relative source intensity at $\phi$ also known as air profile, $\alpha(\epsilon)$ is the mass absorption coefficient for water, $D'(t,\phi)$ is the object density at a position t along beam angle $\phi$, and $\epsilon$ is the beam energy.

The data for tomographic reconstruction is the line integral in the exponent of this equation, hereinafter referred to as $D(\phi)$. If the mass absorption coefficient of water were either energy independent or a constant function of energy, $D(\phi)$ would be trivial to recover. However, the mass absorption coefficient of water is not well approximated by a constant over the non-zero range of the normalized intensity spectra of the source combined with the spectral response to the detector. Because all the functions within the outer integral are positive, semi-definite and the exponential is a monotonic function of $D(\phi)$, an invertible, nonlinear relationship exists between $D(\phi)$ and the detected intensity $I(\phi)$. The necessary correction, then, is this inverse relationship. This relationship may be obtained empirically by a tune-up procedure involving a scan of a water phantom in which coefficients of the polynomial of the beam hardness correction means are adjusted to force a flat response. Mathematically, this can be indicated as:

$$D(\phi) = P_{[I(\phi) - l \; n J(\phi)]} \quad (14)$$

where $P_n$ in the preferred embodiment is a fourth order polynomial. Such a tune-up scan can be made for each flat filter to be used within the beam and the corresponding coefficients for the polynomial stored.

The coefficients of the polynomial are dependent on both the beam spectra and the mass absorption coefficient. When a material with a mass absorption coefficient significantly different from the mass absorption coefficient of water, such as a shaped filter is introduced, equation 13 may be represented as:

$$I(\phi) = \ln \int_0^\infty I^o(\epsilon) J(\phi) e^{-[\alpha(\epsilon) D(\phi) + \beta(\epsilon) T(\phi)]} d\epsilon \quad (15)$$

where $T(\phi)$ is a line integral of the filter density as a function of ($\phi$) and, $\alpha(\epsilon)$ is the mass absorption function of the filter material. This equation shows that the detected intensity is a nonlinear function of both $D(\phi)$ and the line integral of the filter density $T(\phi)$. However, the same type of invertible relationship between $D(\phi)$ and the detected intensity $I(\phi)$ exists as in the water-like material scan set forth in equation 13. Further, because the shape of the filter and the material of which it is made is generally known, $T(\phi)$ is generally readily determined. Accordingly, equation 15 can be written as:

$$I(\phi) = \ln \int_0^\infty (I^o(\epsilon) e^{-\beta(\epsilon) T(\epsilon)}) J(\phi) e^{-\alpha(\epsilon) D(\phi)} d\epsilon \quad (16)$$

From equation 16, it can be seen that the effect of adding an incremental thickness of filter material is the equivalent of altering the intensity and the spectral distribution of the original beam. Thus, a polynomial could be determined for each incremental thickness of filter material. This would invert the integral expression yielding a solution for $D(\phi)$.

However, the polynomial is now a function of two variables, i.e., $T(\phi)$ and $I(\phi)$. This makes the determination of the polynomial coefficients very difficult.

Figure 3:
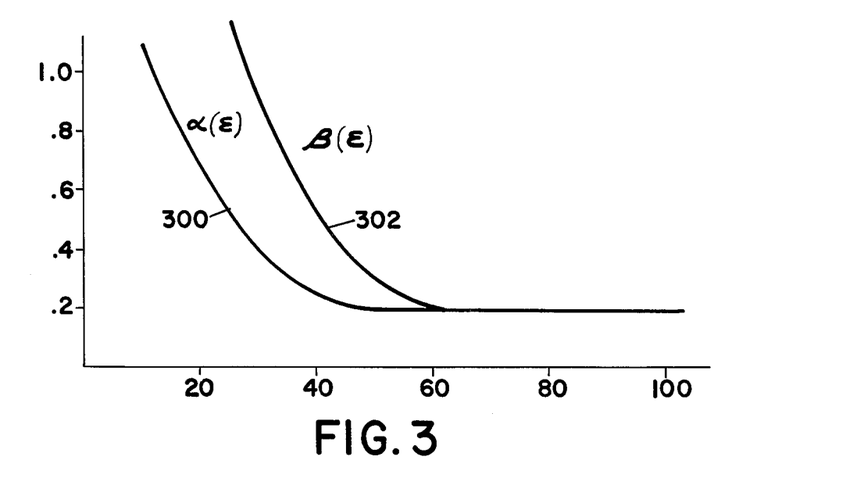
FIG. 3 illustrates the mass absorption coefficient of water and aluminum.

The present invention observes that for a given source spectra, the exit spectra from some filter material thickness $T(\phi)$ can be accurately approximated by a thickness of water. FIG. 3 illustrates the mass absorption coefficients of water 300 and aluminum 302. It will be observed that both functions are monotonic decreasing but differ in their scale of curvature. Over small ranges of energies, however, the absorption coefficient of aluminum can be approximated as the mass absorption coefficient of water shifted relative to the origin, i.e.:

$$\beta(\epsilon) \simeq A_1 + A_2 \alpha(\epsilon) \quad (17)$$

With this approximation, equation 16 becomes:

$$I(\phi) = \ln \int_0^\infty (I^o(\epsilon)e^{-(A_1+A_2\alpha(\epsilon))T(\phi)})J(\phi)e^{-\alpha(\epsilon)D(\phi)}d\epsilon \quad (18)$$

which may be rewritten:

$$I(\phi) = \ln \int_0^\infty e^{-A_1T(\phi)}(I^o(\epsilon)e^{-A_2\alpha(\epsilon)T(\phi)})J(\phi)e^{-\alpha(\epsilon)D(\phi)}d\epsilon \quad (19)$$

The coefficients $A_1$ and $A_2$ give rise to the intensity equivalent and spectral equivalent of the filter material in terms of water. Equation 19 can be rewritten with the energy independent terms removed as follows:

$$I(\phi) \simeq \ln J(\phi) - A_1T(\phi)] + \ln \int_0^\infty I^o(\epsilon)e^{-[D(\phi)+A_2T(\phi)]\alpha(\epsilon)}d\epsilon \quad (20)$$

It is shown above in conjunction with the water phantom or water equivalent materials that the following held true:

$$I(\phi) = \ln \int_0^\infty I(\epsilon)e^{-\alpha(\epsilon)D(\phi)}d\epsilon \quad (21)$$

from which it was shown:

$$D(\phi) = P_{[I(\phi)]} \quad (22)$$

Thus, the inverse of equation 20 can be approximated by the polynomial expression:

$$D(\phi) \simeq P_{[I(\phi) - \ln J(\phi) + A_1(\phi)T(\phi)]} - A_2(\phi)T(\phi)$$

The polynomial in equation 23 is the same polynomial and has the same polynomial coefficient as the polynomials in equations 14 and 22, the coefficients of which are routinely obtained during conventional tune-up procedures. From equation 23, it can be seen that the correction for filters of varying materials and shapes can be obtained by adding a first correction profile, $A_1(\phi)T(\phi)$ to each data line before the beam hardness correction and a second profile $A_2(\phi)T(\phi)$ after the beam hardness correction. Equation 23, it will be observed, is carried out by the circuitry of FIG. 1 previously described.

The invention has been described with reference to the preferred embodiment. Obvious modifications and alterations will be apparent to others upon reading and understanding the preferred embodiment and its theoretical basis. It is our intention to include all such modifications and alterations insofar as they come within the scope of the appended claims of the equivalents thereof.

We claim:

1. An apparatus for reconstructing an image of at least a region of an object positioned in a scan circle comprising:
   a source of radiation having a polychromatic spectrum for irradiating the scan circle with a beam radiation from a plurality of directions;
   at least one radiation detector positioned to receive radiation from said source which beam of radiation has traversed the scan circle along a plurality of paths through the scan circle;
   a radiation filter positioned between the source of radiation and the detector;
   data collection means for collecting data indicative of the intensity of radiation received by said at least one radiation detector along the plurality of paths and organizing the collected data into data lines, said data collection means operatively connected with said at least one detector;
   beam hardness correction means for adjusting said data lines for non-linearities introduced by the polychromatic spectrum of radiation from the source of polychromatic radiation;
   filter correction means for adjusting said data lines for non-linearities introduced by alterations to the polychromatic spectrum of the radiation caused by said radiation filter, said beam hardness correction means and said filter correction means being operatively connected with said data collection means; and
   reconstruction means for reconstructing the data lines into a representation of an image of said region, said reconstruction means being operatively connected with said beam hardness correction means and said filter correction means.

2. The apparatus as set forth in claim 1 wherein said beam hardness corrrection means adjusts said data lines as a function of the mass absorption coefficient of water; and wherein
   said filter correction means adjusts said data lines as a function of the mass absorption coefficient of water.

3. The apparatus as set forth in claim 1 wherein said beam hardness correction means operates on said data lines with a polynomial, said polynomial is so chosen that a uniform image is reconstructed from a scan of a uniform mass of a reference material placed in the scan circle; and wherein
   said filter correction means comprises a first means for altering said data lines before the data lines are operated on with the polynomial and a second means for altering said data lines after the data lines are operated on with said polynomial.

4. The apparatus as set forth in claim 3 wherein said first altering means comprises a first memory means for storing a table of values and a first adding means for adding values from said first memory means to said data lines; and wherein
   said second altering means comprises a second memory means for storing a table of values and a second adding means for adding values from said second memory means to said data lines.

5. The apparatus as set forth in claim 4 wherein said source of radiation produces a generally fan-shaped swath of radiation; and wherein said data collection means organizes the data such that each of said plurality of data lines corresponds to received radiation traversing the scan circle along one substantially fan-shaped array of paths, said plurality of data lines corresponding to differently, angularly oriented fan shaped arrays of paths, and data along each data line being indexed by angular positions of corresponding radiation paths within the fan-shaped array of paths; and wherein said first memory means is addressed by said angular positions; and wherein said second memory means is addressed by said angular positions.

6. The apparatus as set forth in claim 5 wherein said first memory means stores a table of first values corresponding to said angular positions and said second memory means stores a table of second values corresponding to said angular positions, said first and second values being functions of (i) the intensity of radiation received by said at least one detector with air in the scan circle and the radiation filter in place, (ii) the intensity of radiation received by said at least one detector with air in the scan circle and the radiation filter removed, (iii) the intensity of radiation received by said at least one detector with said reference material in the scan circle and the radiation filter in place, and (iv) the intensity of radiation received by said at least one detector with said reference material in the scan circle and the radiation filter removed.

7. The apparatus as set forth in claim 5 wherein said first memory means stores a table of first values corresponding to said angular positions, and said second memory means stores a table of second values corresponding to said angular positions, said first and second values being functions of (i) the intensity of radiation received by the at least one detector with air in the scan circle and the radiation filter removed, (ii) the intensity of radiation received by the at least one detector with air in the scan circle and the radiation filter in place; and wherein said second values are further functions of said first values.

8. The apparatus as set forth in claim 1 wherein said radiation filter is positioned between said source and said scan circle, whereby the filter reduces the radiation dosage impinging upon objects in the scan circle.

9. The apparatus as set forth in claim 8 wherein said radiation filter comprises a block of filter material having a generally parabolic cutout, said parabolic cutout having a center axis.

10. The apparatus as set forth in claim 9 wherein said source of radiation provides a generally fan shaped beam of radiation, said fan shaped beam having two edge portions which are generally tangential to said scan circle, and a central axis intersecting generally the center of the scan circle, said radiation filter being positioned in such a manner that the axis of the parabolic cutout is coincident with said central axis.

11. The apparatus as set forth in claim 9 wherein said filter material is selected from the class consisting essentially of beryllium, aluminum, sulphur, calcium, titanium, erbium, copper, and compounds and alloys thereof.

12. An apparatus for reconstructing an image of at least a region of an object positioned in a scan circle comprising:

a source of radiation having a polychromatic spectrum for irradiating the scan circle from a plurality of directions with a generally fan-shaped array of radiation having an apex generally at the source of radiation;

at least one radiation detector positioned to receive radiation from said source of radiation which has traversed the scan circle;

a radiation filter for altering the polychromatic spectrum of the radiation, comprising a body of filter material, said body having a generally parabolic recess therein, said parabolic recess having a central axis, said body being disposed between said source and said scan circle with said central axis in line with the apex of the fan-shaped array and the center of the scan circle;

data collection means for collecting data indicative of the intensity of radiation received by said at least one detector and organizing the collected data into data lines, said data collection means operatively connected with said at least one detector;

filter correction means for adjusting said data line for nonlinearities introduced by alterations to the polychromatic spectrum of the radiation caused by said radiation filter, said filter correction means being operatively connected with the data collection means; and reconstruction means for reconstructing the adjusted data lines into a representation of an image of said region, said reconstruction means being operatively connected with said filter correction means.

13. The apparatus as set forth in claim 12 wherein the surface of the parabolic recess is defined generally by the equation:

$$y = \frac{2b\alpha R \cos\theta/2}{\beta \left(\frac{2\alpha R}{\beta} \sin\frac{\theta}{2} + r \tan\frac{\theta}{2}\right)^2} x^2$$

where $\alpha$ is the mass attenuation coefficient of the filter body, R is the radius of the scan circle, $\beta$ is the mass attenuation coefficient of water, r is the spacing between the fan apex and the parabolic recess, $\theta$ is the fan angle of the fan-shaped array, b is a scaler between 1 and 6, and x and y are rectangular coordinates.

14. The apparatus as set forth in claim 13 above, where b is generally 2.

15. The apparatus as set forth in claim 13 where b is generally 4.

16. A shaped radiation filter for a tomographic scanner comprising a body of filter material, having a parabolic recess therein.

17. The shaped filter as set forth in claim 16, wherein the parabolic recess is defined by $$y = ax^2$$

where a is in the range of 0.01 to 10.

18. The apparatus as set forth in either of claims 12 and 16 wherein said filter material is aluminum.

19. The shaped filter as set forth in either of claims 12 and 16 wherein said filter material is selected from the class consisting essentially of beryllium, aluminum, sulphur, calcium, titanium, erbium, copper, and compounds and alloys thereof.

20. The apparatus as set forth in claim 1 wherein said radiation filter includes a body of beryllium oxide.

* * * * *